United States Patent
Delcomyn et al.

(10) Patent No.: US 7,429,556 B2
(45) Date of Patent: Sep. 30, 2008

(54) UNIVERSAL HALIDE-ENHANCED DECONTAMINATING FORMULATION

(75) Inventors: Carrie Delcomyn, Lynn Haven, FL (US); Michael Henley, Panama City, FL (US)

(73) Assignee: Applied Research Associates, Inc., Albuquerque, NM (US)

( * ) Notice: Subject to any disclaimer, the term of this patent is extended or adjusted under 35 U.S.C. 154(b) by 307 days.

(21) Appl. No.: 10/693,194

(22) Filed: Oct. 23, 2003

(65) Prior Publication Data

US 2005/0090419 A1 Apr. 28, 2005

(51) Int. Cl.
*C11D 3/395* (2006.01)

(52) U.S. Cl. .................. 510/372; 510/110

(58) Field of Classification Search .......... 510/110, 510/372

See application file for complete search history.

(56) References Cited

U.S. PATENT DOCUMENTS

| 4,822,512 A | 4/1989 | Auchincloss |
| 2001/0008879 A1 * | 7/2001 | Willey ............... 510/372 |

FOREIGN PATENT DOCUMENTS

| WO | WO 92/15334 | * | 9/1992 |
| WO | WO 99/59924 | * | 11/1999 |

OTHER PUBLICATIONS

Product information sheeets, Dow Chemical Corp. 2002. No month available.*

* cited by examiner

*Primary Examiner*—John R Hardee
(74) *Attorney, Agent, or Firm*—Dinsmore & Shohl, LLP; Monika J. Hussell

(57) ABSTRACT

The disclosed invention is a method for the production of a universal decontaminant solution comprised of at least one oxidant and halide salt for neutralizing chemical toxicants that include organosulfur and organophosphorus-containing compounds, such as those found as pesticides, herbicides, or chemical warfare agents, as well as providing disinfection capability against viruses, bacteria, spores, fungi, toxins, and those classified as biological warfare agents. The overall generation and application of the decontaminant solution creates an unexpected synergistic effect toward rates of detoxification, whereas in most cases where the same oxidants were used individually, the same result would not be achieved. A method for the in situ generation of hypochlorous acid and hypochlorite by a monopersulfate compound and alkali metal chloride salt is also described.

12 Claims, No Drawings

UNIVERSAL HALIDE-ENHANCED DECONTAMINATING FORMULATION

FEDERAL RESEARCH STATEMENT

The U.S. Government has a paid-up license in this invention and the right in limited circumstances to require the patent owner to license others on reasonable terms as provided for by the terms of contract F0863798C6002 awarded by the Untied States Department of the Air Force, Air Education and Training Command.

FIELD OF THE INVENTION

The present invention relates to a decontaminating formulation for neutralizing toxic chemical substances and providing disinfection capability towards biologicals. More specifically, the disclosed invention is a universal decontaminant solution comprised of at least one oxidant combined with at least one halide salt for neutralizing chemical toxicants that include organosulfur and organophosphorous-containing compounds, such as those found as pesticides, herbicides, or chemical warfare agents, as well as providing disinfection capability against biological agents.

BACKGROUND OF THE INVENTION

An increase in domestic and foreign terrorist threats associated with the production and dissemination of weapons of mass destruction in recent years has resulted in concern for both civilians and the armed forces in needing readily available universal decontaminant capabilities.

Some decontamination solutions presently available for the destruction of chemical warfare agents include Super Tropical Bleach (STB), a highly corrosive hypochlorite-based alkaline solution, and DS2, which possesses highly toxic ingredients of diethylenetriamine and ethylene glycol monomethyl (EGM) ether. These decontaminants have drawbacks in that they present hazards to the handler(s) and surface materials. The high alkalinity of hypochlorite-based STB and toxic properties of DS2 hinders their practical use for decontamination of sensitive equipment, as well as producing large volumes of hazardous waste products that are difficult to dispose of by environmentally acceptable means.

Recent efforts to develop more user-friendly decontaminants have focused on using strong oxidant applications such as organic and inorganic peracids, activated hydrogen peroxide, and peroxygen compounds.

For example, U.S. Pat. No. 4,850,729 discloses a formulation using peracids (e.g. percarbonate, perborate, persilicate or perphosphate) that are capable of releasing hydrogen peroxide in solution. In combination, an iron bearing clay is utilized as an activator for hydrogen peroxide to generate reactive radical species within the formulation for the purpose of achieving chemical decontamination. Similarly, U.S. Pat. No. 6,245,957 describes the generation of the peracid percarbonate by combining urea hydrogen peroxide with potassium bicarbonate. The invention disclosed in U.S. Pat. No. 6,143,088 also utilizes a peracid formulation in the presence of a cationic surfactant for the destruction of organophosphate and organosulfur compounds. In comparison to reactivity of a peroxygen compound of monoperphthalate, the described formulation was equivalent in reactivity effectiveness in the destruction of the organophosphate agricultural pesticide, Paraoxon. Another alternative peracid oxidant, perborate, is reported to degrade organophosphorous-containing compounds in slightly alkaline conditions as reported by Cristau et al. Lab. Chim. Org. 458, 712 (1991). Although these inventions make use of peracid oxidants, they do not reveal any effectiveness toward biological agents.

As reported by Yang et al. Chem. Rev. 92, 1729 (1992), another peroxygen compound, monopersulfate (found within a triple salt combination sold commercially by DuPont under the trademark name of Oxone®), was evaluated as a decontaminant, but achieved degradation of only mustard (HD) and VX chemical agents under extremely acidic conditions. Biological disinfection capability was similarly described in U.S. Pat. No. 5,186,946 with the use of monopersulfate in the presence of sulfamic and malic acids and polyethylene glycol, but also under acidic conditions.

Other multi-component oxidant systems that utilize either hydrogen peroxide and/or include monopersulfate as a peroxygen compound have targeted decontamination of both chemical and biological warfare (CBW) agents. Both compounds are disclosed in U.S. Pat. No. 6,569,353 to which, similar to U.S. Pat. No. 4,850,729, forms of iron are added to activate the peroxide species. The oxidants are also described in surfactant-based formulations of U.S. Pat. No. 6,369,288 and U.S. Pat. No. 6,566,574.

While the majority of these formulations provide aforementioned oxidants in the presence of other compounds, none incorporate a metal (alkali, alkaline earth, or transition) halide salt as a reactive source, nor disclose the combination as creating a synergistic reactive effect towards both chemical and biological toxicants.

French Patent 1,568,919 was found to disclose a sterilization method for baby bottles that utilized monopersulfate in conjunction with a single halide salt (sodium chloride) in a preferred neutral pH range of 6.5 to 7.5. The aqueous sterilizing formulation involved the additional of small amounts of viscous corn oil and magnesium stearate, which served to create an antistatic powdered base for application. Although tested for disinfection of pathogenic biologicals, its application and effect towards toxic chemical neutralization was not covered.

A preferred embodiment of the present invention is inclusive of a formulation example that provides for the in situ generation of powerful oxidative active chlorine species such as in the form of hypochlorous acid and/or hypochlorite species, but within non-corrosive, neutral pH conditions. The species can be produced in the preferred embodiment by combining an oxidant of alkali metal salt form of monopersulfuric acid (from here forward termed 'a monopersulfate compound') with an alkali metal chloride salt (e.g. sodium chloride) in the presence of a buffer capable of a maintaining a neutral pH range (e.g. sodium bicarbonate).

The generation of oxidants and/or other similar species in situ is unique compared to existing technologies, including the generation of oxidants by more costly electrochemical means. The MIOX Corporation has recently marketed an alternative generation of hypochlorite involving the direct electrolysis of sodium chloride in water to produce a mixture of oxidants believed to include hypochlorite, hypochlorous acid, chlorine dioxide, hydrogen peroxide, ozone, and other short-lived species for the disinfection of drinking water. Numerous case studies conducted in the drinking water industry with the MIOX technology demonstrated that treating water with electrochemically generated mixed oxidants maintained a more stable chlorine residual in distribution systems as compared to treatment by chlorine gas or bleach, indicated a measurable reduction in oxidant demand (possessing approximately 1.4 times more oxidizing power than chlorine alone), and significantly reduced biofilm accumulation in distribution systems.

Additionally, studies performed by the University of North Carolina in conjunction with the U.S. Center for Disease Control reported that electrochemically generated mixed oxidants' can achieve more than 99.9% inactivation of pathogenic *Cryptosporidium parvum* oocyst and surrogate *Clostridium perfringen* spores, which are highly resistant to kill by application of chlorine alone. Another study by Finch et al. Water Quality Technology Conference, Denver (1994) involving the combination of ozone and free chlorine for effective inactivation of *Crytosporidium* supported the theory of synergistic activity involving the electrochemically generated mixed oxidants to selectively target different sites on or in the highly resistant ooysts.

In situ generated oxidants by the addition of halides to a monopersulfate solution has been reported within the paper and pulp industry for the purpose of delignifying and brightening pulp while retarding effects of cellulose decomposition present in the use of more aggressive oxidants such as ozone ($O_3$). The process was conducted at low acidic pH values in which the addition of chloride to monopersulfate generated chlorine ($Cl_2$), accelerating the rate of lignin degradation in comparison to depolymerization of cellulose material. In situ generation of dioxirane compounds (caused by the addition of ketones to a monopersulfate solution) were also compared to halide-monopersulfate process for serving the same purpose. Dioxiranes are also known powerful oxidants capable of transforming chloride into hypochlorite as reported by Montgomery J. Am. Chem. Soc. 96, 7820 (1974) and Edwards et al. Photochemistry and Photobiology 30, 63 (1979). However, the use of a monopersulfate-halide and/or monopersulfate-dioxirane-halide formulation for CBW agent decontamination has not yet been identified in the prior art.

Although the sodium salt of hypochlorite can be typically found in commercial bleach, the active species are based in highly alkaline hydroxide (approximately pH 12) and can therefore be extremely destructive to materials. Besides possessing these corrosive properties, commercial bleach solutions are known to decompose upon storage, thus diminishing the reliability of their potency if used as a decontaminating solution. However, bleach is capable of serving as a dual disinfectant because the presence of hydroxide promotes hydrolysis, and the hypochlorite species serve as strong oxidants, exemplified by its use for the decontamination of chemical agents as described by Yang et al. Chem. Rev. 92, 1729 (1992). Aqueous bleach has been shown to react rapidly with the P-S bond via oxidative-promoted hydrolysis with oxidation also at the tertiary amino group.

Therefore, there is a need in the art to generate a stable reactive decontaminating formulation capable of universal decontamination of chemical and biological toxicants. The combination of a halide salt with an oxidant, as set forth below, will create such an enhanced reactive solution. Powerful active forms of chlorine, such as hypochlorite species, can also be generated in situ by the method of the present invention without electrochemical means and without the need for a caustic base.

SUMMARY OF THE INVENTION

Accordingly, it is an object of the present invention to provide an environmentally friendly universal decontaminating solution for the rapid neutralization of toxic substances based upon the combined formulation of one or more oxidants with one or more alkali metal, alkaline earth metal, or transition metal halide salts (herein referred to as a halide salt or a halide). The effective and versatile formulation eliminates, or greatly minimizes, the impacts of toxicity and corrosiveness to materials caused by, and environmental burdens associated with formulating, many of the prior art universal decontaminant solutions.

The combination of oxidants and halide salts in a water-based solution enhances the oxidative potential of the decontamination formulation and creates an unexpected synergistic effect for substantially increased rates of detoxification as compared to oxidants utilized alone. The formulation effectively neutralizes chemical toxicants that include organosulfur and organophosphorus-containing compounds (such as pesticides, herbicides, or chemical warfare agents), and disinfects matter contaminated with viruses, bacteria, spores, fungi, toxins, and those classified as biological warfare agents.

The formulation of the present invention may comprise dilute solutions, with small quantities of oxidant and/or halide, or over a preparation range in which the solubility of either of the component(s) is exceeded in solution. Furthermore, the formulation may be generated over a wide pH range and in a wide range of temperatures, and may include mixtures of oxidants and/or halides.

Although oxidants and halides can be combined in a water-based solution for effective decontamination over a wide pH range, the addition of a buffer, preferably a bicarbonate-based buffer, to maintain neutral pH conditions will allow for a more practical use of the decontaminant, whereas otherwise acidic or alkaline conditions may corrode or adversely effect some equipment and surfaces to which the formulation is applied.

To neutralize thickened chemical warfare agents, co-solvents may be added to enhance solvation properties of the formulation, as well as the addition of surfactants that provide wetting properties when the solution is placed in contact with contaminated surfaces.

Reagents used for generation of the formula of the present invention are non-toxic, and can be purchased commercially at low cost. The invention is of particular importance to military operations in which large area decontamination would be needed such as to aircraft, tanks, carrier ships, facilities, equipment, and terrain, as well as related civilian or homeland defense operations that involve decontamination efforts by first-responders. Seawater is an ideal source for the halide salt and water solution of the present invention for naval decontamination operations or operations occurring on or near a seawater source.

The disclosed formulation is primarily described for use as a liquid decontaminant spray, but does not exclude its uses in the form of an aerosol or in a suspended form, such as incorporation into a foam or gel.

DETAILED DESCRIPTION OF THE PREFERRED EMBODIMENTS

The formulation of the present invention comprises, in its most general sense, an oxidant or mixture of oxidants and one or more halide salt(s) in a water-based solution, preferably in a neutral pH carbonate-type buffered water solution, to generate reactive species in which a synergistic effect can be observed by enhanced rates of chemical and/or biological degradation.

Oxidants suitable for use in the present invention must be capable of reacting with halide(s) to create reactive species, and include peroxygen and peracid compounds such as monopersulfate (a compound derived from Caro's acid ($H_2SO_5$) and sold commercially in the form of a triple salt as Oxone® ($2KHSO_5 \cdot KHSO_4 \cdot K_2SO_4$)), or alkali metal salts of persulfuric acid, perborate, peracetate, percarbonate, and/or hydrogen peroxide. More preferably, the oxidant is a monopersulfate compound selected from the group consisting of alkali metal salt forms of peroxymonosulfuric acid alone or in combination with the alkali metal salts of sulfuric or persulfuric acid.

Without limiting the foregoing, dioxirane compounds, which are powerful oxidants that can be generated in situ by the addition of select ketones to a carbonate-type buffered aqueous matrix in the presence of a monopersulfate compound, are a preferred oxidant for use in the present invention. The efficiency of dioxirane oxidative chemistry on numerous substrates is well known, but of particular importance is dioxirane's ability to transform a chloride ion into hypochlorite.

Suitable metal (alkali, alkaline earth, or transition) halide salts for use in the present invention include chloride, bromide, iodide and/or salt sources such as seawater and brine solutions. The unique salt source of seawater provides halide ion concentrations that remain fairly constant relative to one another throughout oceans of the world in a neutral pH range. The chloride ion is the most abundant at a concentration of 0.5 M (19 g/kg), followed by other anions (in decreasing order) of sulfate, bicarbonate, bromide, and silicate, all of which can be utilized without any adverse environmental effects or substantial impact on the effectiveness of the composition of the present invention. It should be noted, however, that extremely high organic or excessive microbial levels within a seawater source would consume a significant level of oxidant of the formulation of the present invention, and would therefore hinder the effectiveness thereof.

Examples of buffers that can be utilized to bring the formulation within a neutral pH range include alkali metal salt forms of carbonate and bicarbonate, or phosphate. Preferably, the solution of the present invention is combined with a buffer to result in a formulation with a pH between 4 and 10, and most preferably pH 6 to 8.5.

Acetonitrile, propylene carbonate, propylene glycol, polypropylene glycol and/or tert-butanol are preferred co-solvents to facilitate solvation of the reagents, and surfactants tetrabutylammonium hydrogen sulfate (TBAHS), Triton-X, and/or cetyltrimethylammonium (CTMA) chloride are preferred to facilitate wetting properties of the formulation.

The following formula serves as a representative schematic of an enhanced oxidant-halide system of a preferred embodiment of the present invention whereby a halide salt ($X^-$) is added to a neutrally buffered aqueous sodium bicarbonate ($NaHCO_3$) system containing oxidant (Ox) to generate the reactive species ($Y_{1,2,3}, \ldots$).

When the formulation of the disclosed invention comprises a chloride halide salt and a suitable buffer, active chlorine species are generated in situ, including but not limited to hypochlorite and/or hypochlorous acid, within neutral pH conditions, effectively enhancing reactivity towards toxic agents.

To begin preparation of a preferred embodiment of the active chlorine species decontaminant of the present invention, a solution of about 0.05-20% w/v bicarbonate-type buffer, dissolved in water, is prepared to which 0.1-40% w/v monopersulfate oxidant is added. Upon initial mixing of components some foaming may occur due to off gassing. After mixing 1-20 minutes, 0.1-40% w/v of chloride, preferably sodium chloride, is added to the mixture. Alternatively, if seawater is utilized as the source of halide salts, monopersulfate can be added directly to the source with or without buffer present. When desired, surfactants and/or co-solvents may be added to the solution at concentrations of about 0.01-15% w/v and 10-80% w/v, respectively.

More preferably, the solution comprises 0.5-10% w/v bicarbonate-type buffer, dissolved in water, to which 1-20% w/v monopersulfate oxidant is added and, after complete mixing, 1-20% w/v chloride salt is added to generate the active chlorine reactive species of a preferred embodiment of the present invention. Surfactants and/or co-solvents may be added to the composition in concentrations of about 0.01-5% w/v and 10-80% w/v, respectively.

The resulting mixture is fairly stable for conducting on-site application within at least 7 hours of preparation for the destruction of chemical and/or biological contaminants. Application can be by methods such as spraying or soaking to achieve contact with contaminated surfaces, followed by a recommended water rinse after decontamination is complete on the treated areas. Examples of types of equipment that can be used for large area decontamination include that similar to basic fire fighting equipment, or the U.S. Army ABC-M12A1 skid-mounted decontamination apparatus, which is capable of supporting foam, aqueous or deicing-like solutions; and the M17 transportable decontaminating system that can draw water from a nearby source to dispense a spray to equipment and vehicles.

The following formula serves as a representation of an in situ generation of dimethyidioxirane (DMDO) with the presence of halide salt pursuant to the teachings of the present invention, whereby the DMDO is generated from acetone ($CH_3COCH_3$) and monopersulfate ($KHSO_5$) in a bicarbonate ($NaHCO_3$) buffered aqueous solution, and the halide salt ($X^-$) is added to form the reactive species ($Y_{1,2,3}, \ldots$) of the present invention.

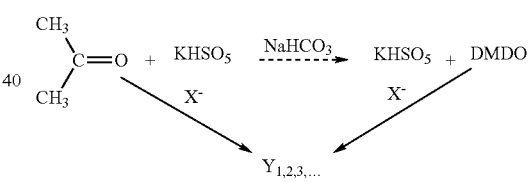

The presence of halides within the decontaminating formulation of the present invention enables a synergistic effect towards degradation rates of a suite of organophosphorous-containing compounds with functionalities such as those found in chemical warfare agents of HD, VX, GD (Soman), and GB (Sarin) as well as degradation rates of biologicals.

The following specific examples are intended to illustrate the effectiveness of the invention.

EXAMPLE 1

As shown in the table below, reactivity towards the degradation of Paraoxon, an organophosphorus pesticide and G-agent simulant, was observed when exposed to a neutral monopersulfate-chloride solution of the present invention, as well as controls chloride alone and monopersulfate alone. The tests were conducted over a period of three hours, using 8.7 umol Paraoxon, at 20-22° C., with the controls and decontaminant present in 100 mL batch systems in deionized water. Batch system concentrations of reactants, as applicable, were 6.2% w/v sodium bicarbonate (12% w/v for pH 8.5 studies), 3.6% w/v sodium carbonate (only for pH 8.5 studies), 10% w/v monopersulfate (Oxone®), 5.4% w/v sodium chloride, and 10% w/v potassium sulfate. The results indicated that chloride alone and monopersulfate alone were considerably ineffective at achieving degradation of this form of substrate, while the combination of the present invention at both pH 7 and pH 8.5 demonstrated a significant increase of 167% and 191% respectively over the independent reagents.

| Batch System | % Paraoxon Degradation | |
|---|---|---|
| | pH 7 | pH 8.5 |
| Sulfate + Chloride Control | 0 | 0 |
| Monopersulfate | 33 | 32 |
| Monopersulfate + Chloride Expected | 33 | 32 |
| Monopersulfate + Chloride Observed | 88 | 93 |
| % Synergy Observed | 167 | 191 |

Only a slight difference was observed between pseudo-first order degradation rates of Paraoxon by the monopersulfate-chloride solutions at pH 7 and pH 8.5, which were measured at 0.0106 $min^{-1}$ and 0.0152 $min^{-1}$, respectively.

A more dilute monopersulfate-chloride system was also tested for degradation of 99+% for HD and VX simulants, where degradation was observed within minutes of exposure. When seawater was used as a halide source for a buffered monopersulfate system, similar degradation patterns towards the functionalities present in H, V, and G-simulants were observed. The nerve agent GB is known to hydrolyze in seawater alone with a half-life of 30 minutes at 25° C. and pH 7.9, and the oxidant-halide formulation of the present invention is not expected to hinder, but rather enhance, the degradation rates of these particular classes of agents.

The stability of the active chlorine species of the present invention was measured in situ from a monopersulfate-chloride system, and compared to that measured from an unbuffered commercial bleach stock. The system for in situ generation of active chlorine species was prepared in 100 mL batch systems with resulting concentrations of each reactant at 10% w/v monopersulfate (Oxone®), 5.4% w/v sodium chloride, and 6.2% w/v sodium bicarbonate, as applicable, balanced in deionized water at 20°-22° C. The active chlorine oxidant measured from a bicarbonate buffered monopersulfate-chloride system was as stable as the hypochlorite content measured from a commercially sold bleach solution when monitored over 7 hours. The amount of in situ generated active chlorine species from the monopersulfate system was 3.9% (w/v), approximately the same concentration found in commercial bleach at 4.3% (w/v). The pH stability of the neutral conditions of the in situ system also remained stable for two days at pH 7.2. This demonstrates an advantage for an in situ generated mixed oxidant solution in that corrosiveness can be controlled for the most part with the use of carbonate-type (or similar type) buffers as opposed to applications of dilute bleach solutions that are based in alkaline hydroxide.

The distribution of hypochlorous acid (HOCl) to hypochlorite ($OCl^-$) species generated in situ in the monopersulfate-chloride system was essentially equal in proportion within a neutral pH range, with only a minor amount of chlorate ($ClO_3^-$) measured as a decomposition product. This decomposition product is a common occurrence being also measured in various commercial bleach stock solutions. Overall mass recovery of chloride species measured in the monopersulfate-chloride system, relative to controls, began at 99.7% with a gradual decrease over 7 hours to 92.5%, likely due to some volatility of reactive species over time. It should be noted that the measurement of hypochlorite species in this system does not exclude the potential presence of other unidentified reactive species that play a role in the synergistic effect observed towards chemical and biological substrates.

EXAMPLE 2

For biological studies, the following table shows a monopersulfate-chloride system that achieved 7-log inactivation of *Bacillus thuringiensis* spores (an anthrax simulant) in 50 mL systems at 20-22° C., within 10 minutes of exposure, exceeding the kill efficiency of buffered monopersulfate alone. System concentrations of each reactant, as applicable, were 10% w/v monopersulfate (Oxone®), 5.4% w/v sodium chloride, 6.2% w/v sodium bicarbonate, and 10% v/v acetone (for generation of a dimethyl dioxirane (DMDO) in the presence of buffered monopersulfate), all at pH 7.4.

| Batch System | Inactivation 10 mins. |
|---|---|
| Bicarbonate Control | 0 |
| Chloride Control | 0 |
| Monopersulfate | 99.9185% |
| Monopersulfate + Chloride | >99.99999% |
| Acetone + Monopersulfate (DMDO) + Chloride | >99.99999% |

The in situ generation of triiodide was also measured from a system to which iodide salt was added to a dilute aqueous solution of buffered monopersulfate. It is known that oxidized species of bromide and iodide are powerful disinfectants.

The disclosed formulation method has the advantage of providing a more effective chemical and biological decontaminant in that reactions can be achieved at increased rates and milder conditions with addition of halide salt to the system. The disclosed invention allows for a formulation that can be effectively utilized within a non-corrosive neutral pH range, resulting in an ideal solution that can be applied to various contaminated surfaces. However, the halide-enhanced formulation of the present invention is not limited to the use or presence of a buffer.

We claim:

1. A composition consisting of:

one or more oxidants, at least one of which is selected from the group consisting of: a monopersulfate compound in the forms derived from alkali metal salt of peroxymonosulfuric acid alone or in combination with the alkali metal salts of sulfuric or persulfuric acid; perborate; peracetate; percarbonate; hydrogen peroxide; and dioxirane compounds, wherein said oxidants are present in the composition in a concentration range of about 0.1-40% w/v;

one or more halides, at least one of which is selected from the group consisting of an alkali metal and an alkaline earth or transition metal halide salt, wherein said halides are present in the composition in a concentration range of about 3-40% w/v;

a buffer capable of bringing the composition to a pH in the range of about 4 to about 10, wherein said buffer is present in the composition in a concentration range of about 0.05-20% w/v; and water.

2. The composition of claim 1 wherein the buffer is selected from the group consisting of alkali metal salt forms of carbonate and bicarbonate, and phosphate.

3. The composition of claim 1 having a pH of between about 6 and about 8.5.

4. The composition of claims 1 or 2 wherein the oxidant(s) are present in the composition in a concentration of about 1-20% w/v, the halide(s) are present in the composition in a concentration of about 3-20% w/v, and the buffer is present in the composition in a concentration range of about 0.5-10% w/v.

5. A composition comprising:
   one or more oxidants, at least one of which is selected from the group consisting of: a monopersulfate compound in the forms derived from alkali metal salt of peroxymonosulfuric acid alone or in combination with the alkali metal salts of sulfuric or persulfuric acid; perborate; peracetate; percarbonate; hydrogen peroxide; and dioxirane compounds, wherein said oxidants are present in the composition in a concentration range of about 0.1-40% w/v;
   a buffer selected from the group consisting of alkali metal salt forms of carbonate, capable of bringing the composition to a pH in the range of about 4 to about 10, wherein said buffer is present in the composition in a concentration range of about 0.05-20% w/v; and
   sea water.

6. The composition of claim 5, further comprising one or more cosolvents; and one or more surfactants.

7. The composition of claim 6 wherein the oxidants are present in the composition in a concentration of about 1-20% w/v, the surfactants are present in the composition in a concentration of about 0.01-5% w/v, the co-solvents are present in the composition in a concentration of about 10-80% w/v, and the buffer is present in the composition in a concentration range of about 0.5-10% w/v.

8. The composition of claim 6 wherein
   at least one of the cosolvents is selected from the group consisting of acetonitrile, propylene carbonate, propylene glycol, polypropylene glycol and tert-butanol; and
   at least one of the surfactants is selected from the group consisting of tetrabutylammonium hydrogen sulfate (TBAHS), octylphenol ethoxylate, and cetyltrimethylammonium chloride (CTMA).

9. The composition of claim 5 wherein the oxidant(s) are present in the composition in a concentration of about 1-20% w/v and the buffer is present in the composition in a concentration range of about 0.5-10% w/v.

10. A composition consisting of:
    one or more oxidants, at least one of which is selected from the group consisting of: a monopersulfate compound in the forms derived from alkali metal salt of peroxymonosulfuric acid alone or in combination with the alkali metal salts of sulfuric or persulfuric acid; perborate; peracetate; percarbonate; hydrogen peroxide; and dioxirane compounds, wherein said oxidants are present in the composition in a concentration range of about 0.1-40% w/v;
    one or more halides, at least one of which is selected from the group consisting of an alkali metal and an alkaline earth or transition metal halide salt, wherein said halides are present in the composition in a concentration range of about 0.1-40% w/v;
    a buffer selected from the group consisting of alkali metal salt forms of carbonate and bicarbonate, capable of bringing the composition to a pH in the range of about 4 to about 10, wherein said buffer is present in the composition in a concentration range of about 0.05-20% w/v;
    one or more cosolvents;
    one or more surfactants; and
    water.

11. The composition of claim 10, wherein the oxidant(s) are present in the composition in a concentration of about 1-20% w/v, the halide(s) are present in the composition in a concentration of about 3-20% w/v, the surfactant(s) are present in the composition in a concentration of about 0.01-5% w/v, the co-solvent(s) are present in the composition in a concentration of about 10-80% w/v, and the buffer is present in the composition in a concentration range of about 0.5-10% w/v.

12. The composition of claim 10 wherein
    at least one of the cosolvents is selected from the group consisting of acetonitrile, propylene carbonate, propylene glycol, polypropylene glycol and tert-butanol; and
    at least one of the surfactants is selected from the group consisting of tetrabutylammonium hydrogen sulfate (TBAHS), octylphenol ethoxylate, and cetyltrimethylammonium chloride (CTMA).

* * * * *

UNITED STATES PATENT AND TRADEMARK OFFICE
CERTIFICATE OF CORRECTION

PATENT NO.       : 7,429,556 B2
APPLICATION NO.  : 10/693194
DATED            : September 30, 2008
INVENTOR(S)      : Delcomya et al.

It is certified that error appears in the above-identified patent and that said Letters Patent is hereby corrected as shown below:

Column 6, line 36-45, delete formula, and replace with formula as shown:

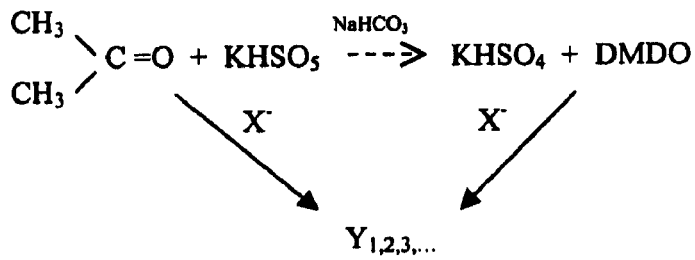

Signed and Sealed this

Eighteenth Day of November, 2008

JON W. DUDAS
*Director of the United States Patent and Trademark Office*